US011813091B2

United States Patent

(12) United States Patent
McDuff

(10) Patent No.: US 11,813,091 B2
(45) Date of Patent: Nov. 14, 2023

(54) ANIMATING PHYSIOLOGICAL CHARACTERISTICS ON 2D OR 3D AVATARS

(71) Applicant: Microsoft Technology Licensing, LLC, Redmond, WA (US)

(72) Inventor: Daniel J. McDuff, Cambridge, MA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/107,632

(22) Filed: Feb. 9, 2023

(65) Prior Publication Data

US 2023/0181124 A1 Jun. 15, 2023

Related U.S. Application Data

(63) Continuation of application No. 16/902,047, filed on Jun. 15, 2020, now Pat. No. 11,602,314.

(51) Int. Cl.

| | |
|---|---|
| *A61B 5/00* | (2006.01) |
| *G06N 20/00* | (2019.01) |
| *A61B 5/0205* | (2006.01) |
| *A61B 5/026* | (2006.01) |

(52) U.S. Cl.
CPC ............ *A61B 5/744* (2013.01); *A61B 5/0205* (2013.01); *A61B 5/026* (2013.01); *G06N 20/00* (2019.01)

(58) Field of Classification Search
CPC ....... A61B 5/744; A61B 5/0205; A61B 5/026; G06N 20/00
See application file for complete search history.

(56) References Cited

U.S. PATENT DOCUMENTS

2017/0213473 A1* 7/2017 Ribeira .................... G09B 5/10

* cited by examiner

*Primary Examiner* — Curtis B Odom

(57) ABSTRACT

Systems and methods are directed to animating subtle physiological processes directly on avatars and photos. That is, physiologically-grounded spatial, color space, and temporal modifications may be made to the appearance of an avatar to simulate a physiological characteristic, such as blood flow. More specifically, a frame of a video sequence and a physiological signal may be received. An attention mask may be generated based on the received physiological signal, where the attention mask includes attention weights indicative of a strength of the physiological signal for differing portions of the frame of the video sequence. Accordingly, a pixel adjustment value based on the physiological signal and the attention mask may be generated and applied to an identified pixel in the frame of the video sequence.

20 Claims, 11 Drawing Sheets

116 112 104 120 132 148 108 144 136 130 152 134
$X_{t+2}$ $X_{t+1}$
Model/Structure 124
Model Weights 128
Attention Mask
At
$W_{x,y}$
Color Space Augmentation
Color Mask Weights
$R_t$ $G_t$ $B_t$
xt
Physiological Temporal Signal
Channel Color Coefficients
$R_t$

ANIMATING PHYSIOLOGICAL CHARACTERISTICS ON 2D OR 3D AVATARS

CROSS-REFERENCE TO RELATED APPLICATIONS

This application is a continuation of U.S. patent application Ser. No. 16/902,047, filed on Jun. 15, 2020, the disclosure of which is hereby incorporated by reference in its entirety

BACKGROUND

As avatars become more realistic, their use becomes more widespread and observers tend to find them more trustworthy. However, when avatars are so realistic that small discrepancies become apparent, observers tend to find such avatars repulsive and disconcerting. To make avatars more trustworthy and more realistic, avatars may be rendered to include physiological signals important for creating a more lifelike appearance. While the computer graphics community has contributed valuable methods for applying and magnifying subtle physiological changes to avatars, such methods tend to be suitable only for magnifying signals that are already present in the source material and cannot be easily adapted for animating avatars or images that are initially static.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

An approach for animating subtle physiological processes directly on avatars and photos is provided in accordance with examples of the present disclosure. More specifically, physiologically-grounded spatial, color space, and temporal modifications may be made to the appearance of the avatar that simulates a physiological characteristic, such as blood flow. A physiological signal amplitude, such as a blood flow signal amplitude, is very small and it is difficult for viewers to “see”. However, avatars with physiologically-based blood flow animations are perceived as more anthropomorphic and animated than those without, and manipulating the heart rate of an avatar changes how the avatar is received amongst observers.

In accordance with at least one example of the present disclosure, a method for applying a physiological characteristic to a portion of video is provided. The method may include receiving a frame of a video sequence, receiving a physiological signal, generating an attention mask based on the received physiological signal, wherein the attention mask includes attention weights indicative of a strength of the physiological signal for differing portions of the frame of the video sequence, generating a pixel adjustment value based on the physiological signal and the attention mask, and applying the pixel adjustment value to an identified pixel in the frame of the video sequence.

In accordance with at least one example of the present disclosure, a computer-readable media including instructions is provided. When the instructions are executed by a processor, the instructions cause the processor to receive a frame of a video sequence, receive a physiological signal, generate an attention mask based on the received physiological signal, wherein the attention mask includes attention weights indicative of a strength of the physiological signal for differing portions of the frame of the video sequence, generate an alpha mask for a first color based on the frame of the video sequence, the physiological signal, the attention mask, and a color channel coefficient associated with the first color, and combine the generated alpha mask for the first color with an alpha mask of a second color to generate an output frame.

In accordance with at least one example of the present disclosure, a system for applying a physiological characteristic to a portion of video is provided. The system may include a processor and memory storing instructions, which when executed by the processor, cause the processor to receive a frame of a video sequence, receive a physiological signal, generate an attention mask based on the received physiological signal, wherein the attention mask includes attention weights indicative of a strength of the physiological signal for differing portions of the frame of the video sequence, generate a pixel adjustment value based on the physiological signal and the attention mask, and apply the pixel adjustment value to an identified pixel in the frame of the video sequence.

Any of the one or more above aspects in combination with any other of the one or more aspects. Any of the one or more aspects as described herein.

This Summary is provided to introduce a selection of concepts in a simplified form, which is further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the following description and, in part, will be apparent from the description, or may be learned by practice of the disclosure.

BRIEF DESCRIPTION OF THE DRAWINGS

Non-limiting and non-exhaustive examples are described with reference to the following Figures.

DETAILED DESCRIPTION

Figure 1:
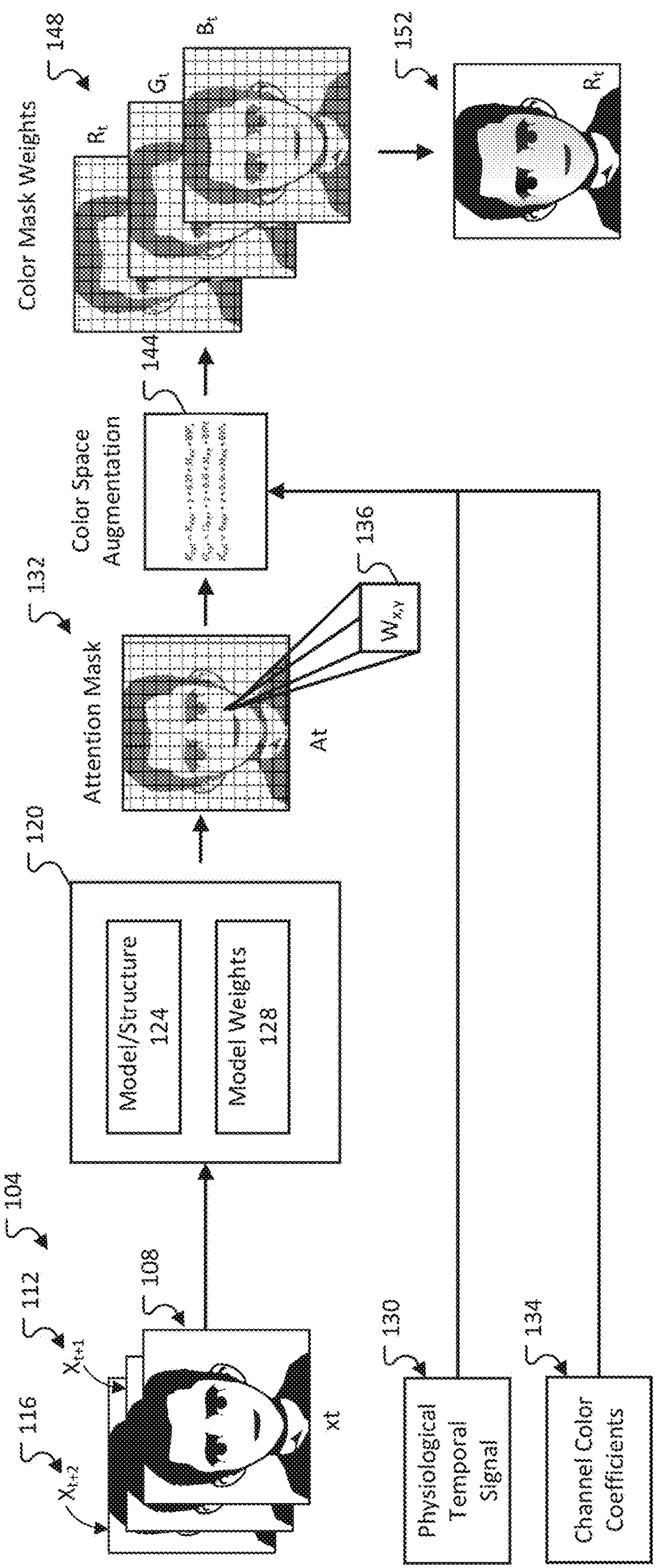
FIG. 1 depicts details of a directed to applying a physiologic characteristic to a video sequence in accordance with examples of the present disclosure.

In the following detailed description, references are made to the accompanying drawings that form a part hereof, and in which are shown by way of illustrations specific embodiments or examples. These aspects may be combined, other aspects may be utilized, and structural changes may be made without departing from the present disclosure. Embodiments may be practiced as methods, systems or devices. Accordingly, embodiments may take the form of a hardware implementation, an entirely software implementation, or an implementation combining software and hardware aspects. The following detailed description is therefore not to be taken in a limiting sense, and the scope of the present disclosure is defined by the appended claims and their equivalents.

There are many properties that create believable avatars such as computer generated, or synthetically generated avatars. What distinguishes the avatar as a healthy person versus a zombie, both of which can move, is the appearance that the avatar is fully alive. Similarly, what distinguishes a video of a person sitting still versus a photograph is subtle motions of the body, such as blinking, breathing or even blushing. As avatars, become more realistic, people find them increasingly trustworthy until they are so realistic that small discrepancies become apparent; at this point people can start to find them repulsive, which is a phenomenon that is referred to at the uncanny valley. Even very small differences in the appearance of an avatar help create a more natural and lifelike appearance. It is further important to consider physiological signals as subtle as variations in blood flow, respiration, and blinking and may take into consideration signals based on external factors such as temperature of the environment and an emotional state of the avatar. While observers may not be able to "see" or identify these changes very easily, such subtle changes influence an observer's perception and acceptance of an avatar, such as accepting the avatar as real. Even though these variations are subtle, modeling the subtle changes on real human data creates a more believable effect than using simple heuristics.

For example, early research on avatars focused on modeling the most obvious behaviors necessary for the avatar to move and communicate, such as: lip syncing, head gestures, and facial expressions. Experiments have shown that people can easily spot when these behaviors have unnatural intensities or dynamics or when there is a mismatch between artificial and human features. Such unnatural intensities or dynamics and mismatched features factors contribute to making a character, such as an avatar, appear to be less trustworthy. Recent work has begun to focus on more subtle aspects of appearance. For example, researchers have started to model blood perfusion patterns in faces with different emotional expressions and developed 3D graphics models of human skin with realistic appearance changes based on the level of blood concentration. However, these approaches do not model dynamic physiological variations, such as perfusion because of blood flow, and/or are not amenable to animating existing avatars, or even photos, in a natural data-driven manner.

One reason that little attention has been paid to modeling subtle aspects of human physiology on avatars is the challenging nature of measuring accurate spatial and dynamic patterns. For example, the peripheral blood flow signal is not spatially uniform across all regions of skin. Most physiological measurement techniques developed in the past have focused on point measurements, like the photoplethysmographic sensors in wearable devices. Thermographic imaging (TI), laser Doppler flowmetry (LDF), and laser Doppler imaging (LDI) have all been used to capture skin blood flow; however, these are not ubiquitous devices. Recent developments in the field of biomedical engineering have led to a suite of techniques termed imaging photoplethysmography (iPPG). These computer vision approaches enable non-contact measurement of blood flow via everyday cameras.

Imaging-PPG algorithms involve analysis of pixel intensities across time from video and an unsupervised or a supervised model to recover physiological signals, such as but not limited to blood volume pulse (BVP), from these observations. In early methods, an aggressive spatial aggregation of pixels was used to boost the signal-to-noise ratio before applying a signal processing technique to recover the physiological signal, such as the BVP signal. As such, such techniques only capture how the intensity of the skin is changing "globally" and not local variations. More recently, spatial maps that model the blood flow, or blood perfusion, which is the rate of change at any tissue region over time, have been proposed. The blood perfusion is proportional to the amplitude of the BVP signal. Some of these approaches use a reference signal from an electrocardiogram or pulse oximeter to map the intensity of the BVP in each video. Others leverage learning-based approaches that when trained on videos of subjects with ground-truth blood pulse measurements, learn attention weights that represent the "strength" of the pulse signal.

In accordance with examples of the present disclosure, the learning-based approach allows for the animation of avatars directly from video frames that may have no physiological signal, such as a blood flow signal, respiratory signal, blood volume pulse, or other physiological signals. As an example of a physiological signal that may be added to a synthetically generated avatar, the peripheral blood volume pulse has a dominant frequency component at the heart rate and a characteristic temporal profile resulting from the way the pressure wave travels from the heart to the periphery of the body and back. The morphology of the waveform contains important information about health and identity. The peripheral blood volume pulse also changes with physiological demands over time and does not follow a simple periodic sinusoidal pattern. In addition, signals based on external factors such as temperature of the environment and an emotional state may be considered. For example, temperature may influence a pulse, blood flow, or respiratory rate; such influence may be reflected in the avatar. Similarly, an emotional state may be provided such that physiological changes (e.g., pulse, blood flow, respiratory rate) associated with different emotional states may be more truly reflected by the avatar.

The effects of pulse, or blood flow, on the body are different from those due to respiration. Respiration is mostly observed via motion or deformation of the body, whereas, changes due to blood flow manifest as color or reflectance changes and only very small motions.

While advances from the computer graphics community have led to impressive physiologically-based models with multiple translucent layers in the skin, these models capture the subsurface scattering that occurs when light interacts with the outer layers of the skin (i.e., epidermis and dermis). Dynamic appearance models of skin built from in-vivo measurements of melanin and hemoglobin concentrations have been proposed. These skin models are like those developed for the purposes of imaging photoplethysmograpy, for analyzing static images of the skin, and for decomposing the images into melanin and hemoglobin layers. While the skin appearance changes related to sweating have been studied, where a models were created that capture the effects of physical changes on light reflected from the skin, such studies have only considered the skin appearance of a single image before and after sweating, instead of capturing the subtle dynamic changes on the face. Accordingly, the addition to accurate spatial profiles and color changes, and then faithfully modeling these temporal dynamics will create a more lifelike avatar.

In addition to modeling a one-dimensional pulse signal, examples presented herein also model how the one-dimensional pulse signal changes the appearance of the face. Many methods for camera-based perfusion measurement are often too noisy to provide spatial maps that capture how the pulse signal varies across the face. Current perfusion measurement from cameras typically uses a reference photoplethysmograpy (PPG) signal to filter noise and amplify the signal in a particular frequency band. They either use a reference signal obtained from spatially averaging many pixels over a larger region or a gold standard pulse oximeter signal from a contact sensor. Attention mechanisms in deep learning have proven to be very effective at creating spatial maps that reflect the weight a pixel contributes toward a given label. For example, such attention mechanisms may be used during image classification to identify regions of an image that contain pixels contributing towards a specific class label. They can also be used to segment regions that have specific dynamic patterns, for example in activity recognition. Instead of using a reference iPPG signal to estimate perfusion, examples of the present disclosure use a deep learning approach which contains an attention mechanism to directly learn which pixels in a facial region are likely to contain a strong iPPG signal, giving us a prior for the blood perfusion through the face.

In examples, a framework for superimposing a physiological signal to an avatar may include, but is not limited to spatial mapping of the physiological signal directly from images or video frames, color space variations based on one or more characteristics of physiological signals, and replication and manipulation of temporal dynamics of the physiological signals. In one example, where the physiological signal may be blood volume perfusion, the framework may include spatially mapping the blood perfusion intensity directly from images or video frames, color space variation based on the absorption profile of hemoglobin and the replication and manipulation of temporal dynamics of the BVP, including the systolic and diastolic waveform characteristics.

In some aspects, empirical results that capture the weight of the physiological signal, such as a blood flow signal, are used to inform color space changes as physiological characteristics vary, such as the variation of the blood volume. While it is often assumed that varying the red color intensity would be a good approach as blood is red in color, the blood pulse signal is present across the visual spectrum and the green channel is most affected by blood flow.

In accordance with examples of the present disclosure, an end-to-end deep convolutional attention network (CAN) may be utilized to create a model for the spatial distribution of blood flow using both temporal and color information. The model may be trained in a supervised manner utilizing videos of subjects with ground-truth physiological signals as labels. The network of the model accurately learns to recover the pulse signals and generalize to new faces. The model may generate learned attention maps which capture variations in the blood flow signal across the face. The trained network can then be used to recover blood perfusion heat maps for new faces, including those of synthetic 2D and 3D avatars. The model does not just learn to segment skin, but rather to place greater weight on pixels with high perfusion signals (e.g., the forehead and cheeks).

As depicted in FIG. 1, details directed to superimposing a physiological characteristic, such as a physiological temporal signal onto an avatar are provided in accordance with examples of the present disclosure. More specifically, a video sequence 104, comprising one or more input images 108, 112, and 116 of a video may be provided to the machine learning model 120. The input images 108, 112, and 116 may correspond to a temporal sequence of images. The video sequence 104 may correspond to video that includes an avatar, rendered for one or more specific purposes, such as providing information to a user. In some examples, the video sequence 104 may correspond to video rendered in real-time such as in response to a user selection. In some examples, the video may include a sequence of images depicting real individuals, where a user wishes to change an existing physiological characteristic of the depicted individual.

The video sequence 104 may be provided to the machine learning model 120; the machine learning model 120 may include but is not limited to a model file 124 and a weights file 128. The artefact created after training a machine learning model and that is used to make predictions on new data is called a model. For example, after training a machine learning model, such as a convolutional attention network (CAN) or other deep neural network (DNN), the machine learning model 120 is output as model file 124 containing the layers of the CAN and as a weights file 128 that includes the various weights to be applied to the machine learning structure stored in the model file 124. In some examples, the machine learning model 120 may be of a file format, as depicted in FIG. 1 and as discussed above. In some examples, the machine learning model 120 may be embodied as another portion of software and/or as a filter imported into a graphics or video processing application to apply a physiological characteristic to an avatar or person depicted in the video sequence 104.

As each frame is provided to the machine learning model 120, the machine learning model 120 may output an attention mask 132. The attention mask 132 may correspond to a mask having a same or similar dimension to that of the input image 108. The attention mask may provide a mechanism for identifying and/or addressing specific pixels of the input image 108 that are to be modified when applying the physiological characteristic to the input image. The attention mask 132 may be based on features extracted by or otherwise identified by the machine learning model 120 based on the input image 108, where such features are identified as areas of or portions of the input image 108 that are to be modified by the physiological characteristic. In examples, the physiological characteristic may be one or more of a blood volume pulse, blushing, blinking, and/or breathing. The attention mask 132 may assign higher pixel weights 136 to skin areas with stronger signals, such as those skin areas of the face that are to be augmented with the physiologic characteristic. Each pixel weight 136 or weighting for each pixel in the attention mask may correspond to a pixel of the input image 108.

A color space associated with the input image 108 may be augmented or modified at 144 utilizing the pixel weights 136 and the physiological temporal signal 130. In examples, the physiological temporal signal 130 may correspond to a blood volume pulse and may be equal to a waveform having an amplitude and frequency. In some examples, the physiological temporal signal 130 may correspond to any physiological characteristic of which can be expressed as a signal, such as a respiratory waveform, a blinking waveform, and a waveform or triggered input causing a user to blush. Alternatively, or in addition, the physiological temporal signal 130 may also include one or more signals that influence physiological characteristics based on external factors such as temperature of the environment and an emotional state. For example, temperature may influence a pulse, blood flow, or respiratory rate; such influence may be reflected in the avatar based on an external factor or parameter. Similarly, an emotional state may be provided as an external factor or parameter such that physiological changes (e.g., pulse, blood flow, respiratory rate) associated with different emotional states may be more truly reflected by the avatar. In some example, the channel color coefficients 134 may be associated with or otherwise based on the physiological temporal signal characteristic. That is, if the physiological temporal signal 130 is associated with a respiratory waveform, or other characteristic, the channel color coefficients 134 would be indicative of that characteristic. In examples, for each color channel, the resulting color channel frame, or alpha mask, may be generated based on the corresponding attention weights obtained from the attention mask, the physiological temporal signal 130, and the channel color coefficients 134. Accordingly, for each frame of the video sequence 104, three color channel frames 148 (e.g., Red, Green, and Blue) may be generated and may be synthesized together to generate the output frame 152, where the output frame 152 is an augmented version of the input image 108 augmented by the physiological temporal signal 130.

Figure 2:
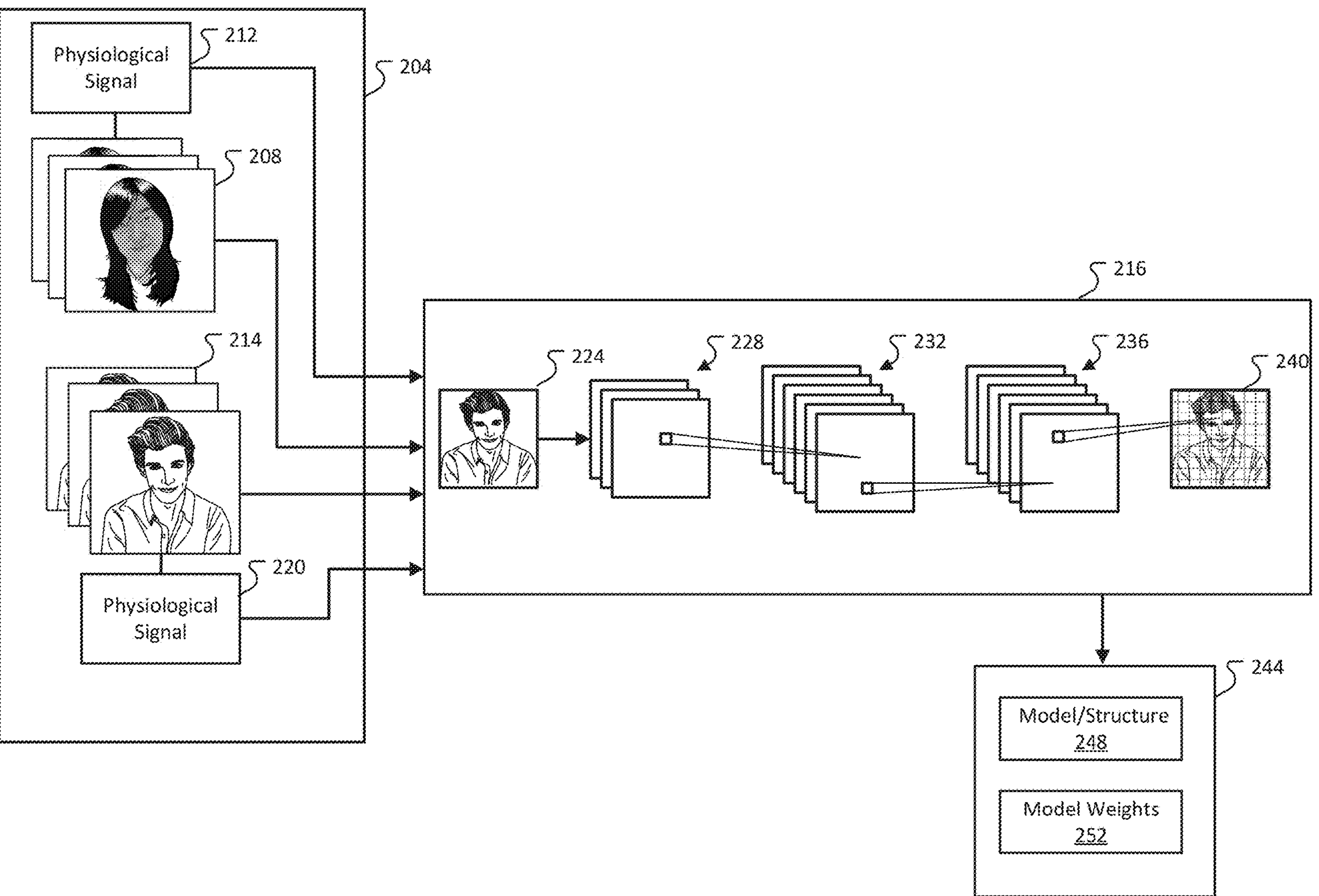
FIG. 2 depicts details directed to training a first machine learning model in accordance with examples of the present disclosure.

FIG. 2 provides additional details with respect to a machine learning structure 216 utilized to build a machine learning model 244 based on training data 204 including video segments, such as video segments 208 and 214 in addition to the physiological signals 212 and 220 and in accordance with examples of the present disclosure. The machine learning structure 216 may be trained with a plurality of video segments 208/214, where each video segment 208/214 includes multiple images/frames. In addition, the machine learning structure 216 may be trained with physiological information specific to each individual depicted in the video segments. For example, the video segment 208 may include multiple frames depicting an individual; the physiological signal 212 received at the machine learning structure 216 is associated with the individual depicted in the video segment 208. As one example, the physiological signal 212 may be a blood volume pulse; such signal may be acquired from one or more devices or sensors, contact or non-contact, utilizing physiological measurement techniques such as photoplethysmographic sensors, thermographic imaging (TI), laser Doppler flowmetry (LDF), laser Doppler imaging (LDI), and/or a pulse oximeter as previously described. Similarly, other physiological signals may include blushing, blinking, and/or respiratory rates and may be acquired with the same or similar sensors or devices. Similarly, other factors influencing physiological characteristics, such as temperature and emotional state may be acquired. As another example, the video segment 214, different from the video segment 208, may include multiple frames depicting an individual; the physiological signal 220 received at the machine learning structure 216 is associated with the individual depicted in the video segment 214. The physiological signal 220 may be a blood volume pulse; such signal may be acquired from one or more devices or sensors, contact or non-contact, utilizing physiological measurement techniques such as photoplethysmographic sensors, thermographic imaging (TI), laser Doppler flowmetry (LDF), laser Doppler imaging (LDI), and/or a pulse oximeter as previously described. Similarly, other physiological signals may include blushing, blinking, and/or respiratory rates and may be acquired with the same or similar sensors or devices. Similarly, other factors influencing physiological characteristics, such as temperature and emotional state may be acquired. The machine learning structure 216 may be trained utilizing the video segments 208 and video segments 214, together with respective physiological signals 212 and 220 and in some cases, the other factors influencing physiological characteristics. It should be understood that the video segment 208, physiological signal 212, video segment 214, and physiological signal 220 are but a portion of the training data 204 utilized to train the machine learning structure 216.

A first frame 224 of the video segment 214 may be received at the machine learning structure 216 for training. The first frame 224 may be subjected to preprocessing, such as but not limited to normalization including subtracting the image mean and normalizing the contrast within the image. The physiological signal 212/220 may be subjected to preprocessing and/or filtering. The machine learning structure 216, in some examples a convolutional attention network which may be trained to recover the physiological signal from the video segments 208 and 214 for example. In some examples, the physiological signal may be a pulse signal that is recovered from one or more of the video segments 208 and 214. Accordingly, once the machine learning structure 216 has been trained, the first three layers 228, 232, and 236 may be used to recover a physiologically specific mask 240 from which the physiological signal for the given frame (e.g., 224) may be recovered. For example, the physiological signal may be blood volume pulse and a recovered blood volume pulse may be recovered from the physiologically specific mask 240, in this case a perfusion mask. Once the machine learning structure 216 has been trained, a machine learning model may be output in a file format including the model structure which is stored in the model file 248 together with the model weights 252.

Figure 3:
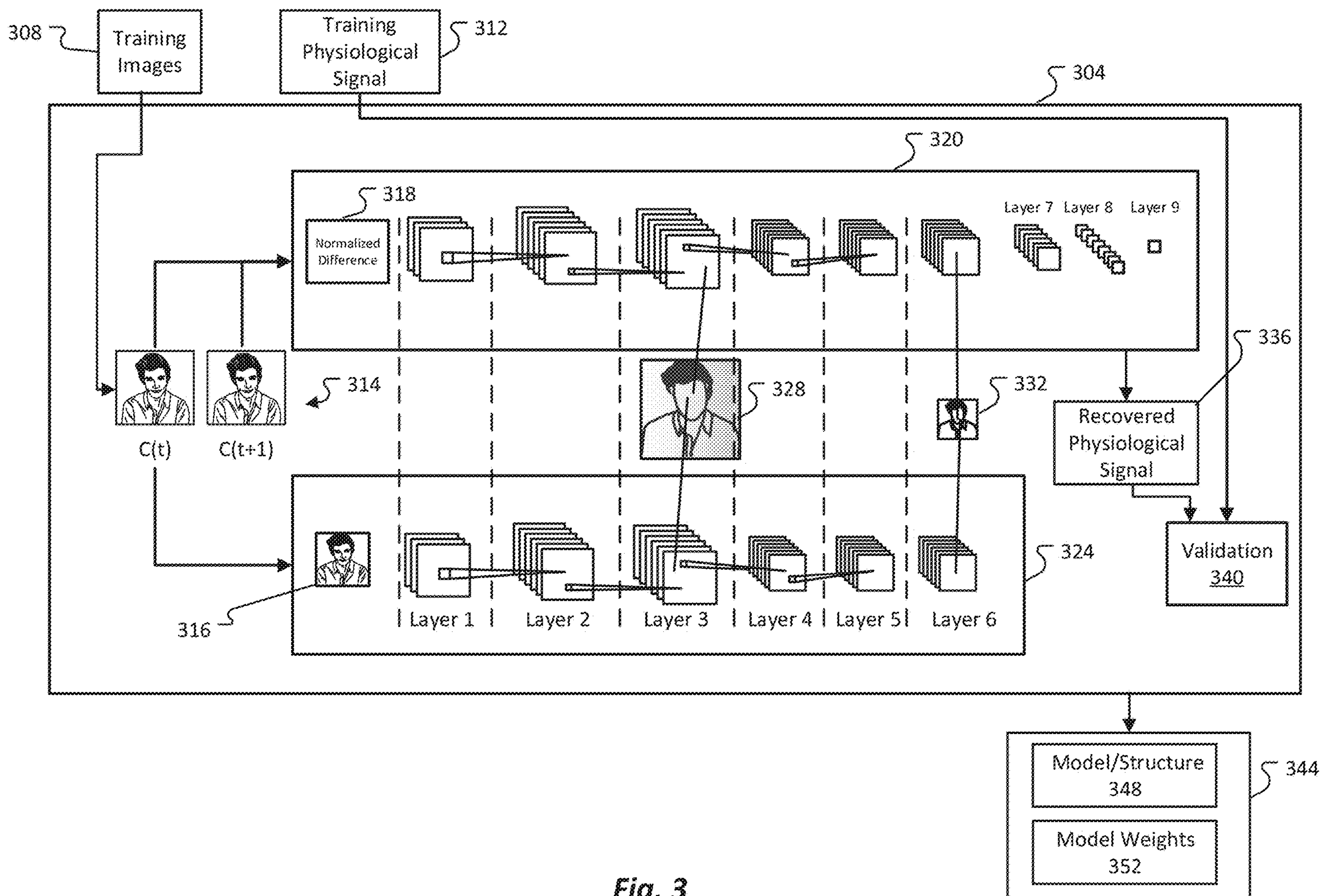
FIG. 3 depicts details directed to training a second machine learning model in accordance with examples of the present disclosure.

FIG. 3 provides additional details directed training a machine learning structure 304 to build a machine learning model 344 based on sample data including the training images 308 and the training physiological signal 312 is provided in accordance with examples of the present disclosure. The machine learning structure 304 may be stored in a file as processor executable instructions such that when a collection of algorithms associated with the machine learning structure 304 are executed by a processor, a machine learning model 344 including various layers and optimization functions and weights is constructed. That is, the various layers comprising the architecture of the machine learning structure 304 may iteratively train utilizing the training images 308 to recover a physiological signal 336 present in the training images 308. The recovered physiological signal 336 may then be validated at 340 by comparing the recovered physiological signal 336 to the known training physiological signal 312 to determine an amount of error. The various layers comprising the machine learning structure 304 and one or more parameters associated with the machine learning structure 304 may be trained to identify and obtain the physiological signal 336. After many iterations, or epochs, the configuration of the machine learning structure 304 (e.g., the various layers and weights associated with each layer) having the least amount of error associated with an iteration may be utilized as the machine learning model 344, where the structure of the machine learning model may be stored in the model file 348 and the weights associated with one or more layers and/or configurations may be stored in the model weights file 352.

In accordance with examples of the present disclosure, the machine learning structure 304 may include two paths; a first path associated with a motion model 320 and a second path associated with an appearance model. The architecture of the motion model 320 may include nine layers with 128 hidden units for example. In addition, an average pooling and hyperbolic tangent may be utilized as the activation functions. The last layer of the motion model 320 may include linear activation units and a mean squared error (MSE) loss. The architecture of the appearance model 324 may be the same as the motion model 320 but without the last three layers (e.g., Layer 7, Layer 8, and Layer 9). In addition to a one-dimensional physiological signal, the machine learning structure 304 may output an attention mask, such as the attention mask 328/332 for each video frame of a video segment. The attention mask indicates which portion or regions of the input image were used to compute the recovered physiological signal, such as the blood volume pulse.

The motion model 320 allows the machine learning structure 304 to differentiate between intensity variations caused by noise, e.g., from motion from subtle characteristic intensity variations induced by the physiological characteristic. The motion representation is computed from the input difference of two consecutive video frames 314 (e.g., C(t) and C(t+1). The ambient illumination may not be uniform on the face and the illumination distribution changes with the distance of the face to the light source and may be affecting the supervised learning approach. Therefore, to reduce these sources of illumination noise, the frame difference is first normalized at 318 using an AC/DC normalization based on the skin reflection model. The normalization may be applied once to the entire video sequence by subtracting the pixel mean and dividing by the standard deviation. In addition, each layer, Layer 1-Layer 5, may be a convolution layer of different or the same size and may be utilized to identify various feature maps utilized through the training of the machine learning structure 304. In examples, the normalization difference 318 may correspond to a normalized difference for three color channels, such as a red, green, and/or blue color channel. Alternatively, or in addition, color spaces other than RGB may be used. For example, color spaces including luminance and chrominance channels (e.g., YUV, Y'UV, YCrCb, Y'CrCb may be used. Similarly, the hue, saturation, and value (HSV) color space may be used. The various layers of the motion model 320 may include feature maps and/or various convolutions of various sizes and color channels.

The appearance model 324 allows the machine learning structure 304 to learn which regions in the image are likely to be reliable for computing strong physiological signals, such as iPPG signals. The appearance model 324 may generate a representation from each input video frame's texture and color information. The appearance model 324 guides the motion representation to recover iPPG signals from various regions included in the input image, and to further differentiate between them from other sources of noise. The appearance model 324 may take as input a single image (C(t) or frame of video. That is, the single frame of video or image 316 may be utilized as an input to the various layers, Layers 1-Layers 6).

The recovered physiological signal 336 may be compared to the training physiological signal 312 and may be validated at 340. Once a satisfactory amount of error is achieved, the machine learning structure 304 may be output as a machine learning model 344 where the structure of the machine learning model 344 may be stored in the model file 348 and the various weights of the machine learning model are stored in a location associated with FIG. 3. Although depicted with a specific deep learning implementation, it should be understood that the machine learning structure may be modified, tuned, or otherwise changed to achieve a greatest amount of accuracy associated with detecting a physiological signal, such as blood volume pulse.

Figure 4:
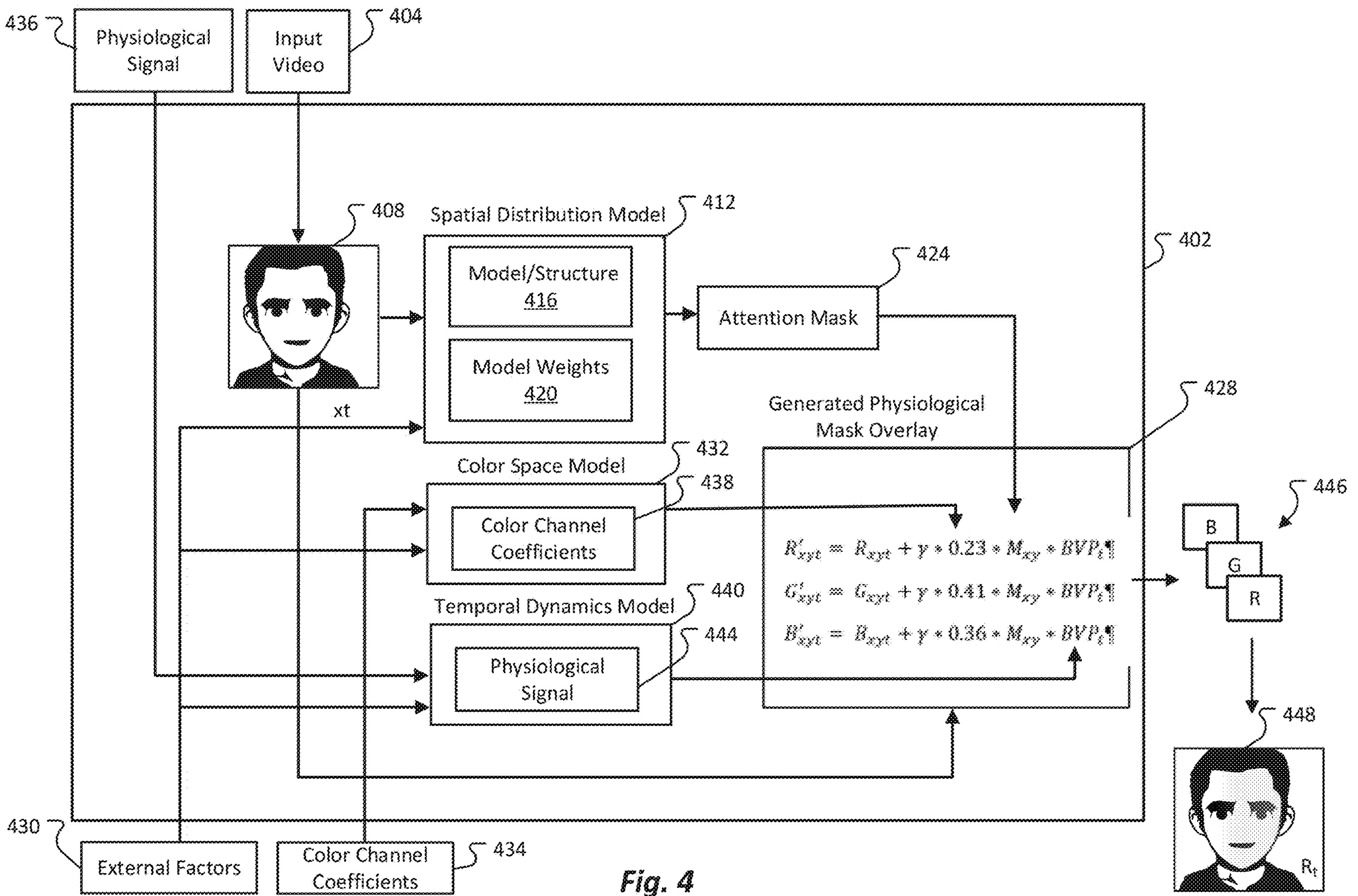
FIG. 4 depicts details directed to applying a physiologic characteristic to a video sequence in accordance with examples of the present disclosure.

FIG. 4 depicts additional details associated with executing a machine learning model 412 and applying or otherwise superimposing a physiological characteristic to one or more frames of an input video segment. That is, a device, such as a computing device 402 may execute, or cause to be executed, a machine learning model 412 to recover one or more attention masks 424 based on an input image 408 from an input video 404. That is, a machine learning model 412, also referred to as a spatial distribution model, may utilize the machine learning model structure in the model file 416 and the model weights 420 to obtain an attention mask 424 that includes at least one weight or scaler for each pixel in the input frame or input image 408. As previously discussed, the attention mask may 424 may correspond to a mask having a same or similar dimension to that of the input image 408. The attention mask 424 may provide a mechanism for identifying and/or addressing specific pixels of the input image 408 that are to be modified when applying the physiological characteristic to the input image. The attention mask 424 may be based on features extracted by or otherwise identified by the machine learning model 412 based on the input image 408, where such features are identified as areas of or portions of the input image 408 that are to be modified by the physiological characteristic. In examples, the physiological characteristic may be one or more of a blood volume pulse, blushing, blinking, and/or breathing. The attention mask 424 may assign higher weights to skin areas with stronger signals, such as those skin areas of the face that are to be augmented with the physiologic characteristic. Each weight or weighting for each pixel in the attention mask may correspond to a pixel of the input image 408. Further, the attention mask may vary with each frame of video.

The computing device 402 may also utilize a color space model 432 to determine and/or apply color channel coefficients 438 to each pixel of the input image 408. In some instances, the color channel coefficients 438 are preprogramed or otherwise included in the color space model 432; in some instances, the color channel coefficients 438 may be provided as an external input, such as the color channel coefficients 434. More specifically, the color channel coefficients 434 and/or 438 may be adjusted or modified based on user and/or machine learning model preference. The color channel coefficients may be specific to the physiological signal 436. For example, where the physiological signal is directed to blushing, the color channel coefficients 434 and/or 438 may be different from the color channel coefficients 434 and/or 438 that are specific to blood volume pulse. In addition to the color space model 432 and the spatial distribution model, also referred to as the machine learning model 412, the computing device 402 may execute a temporal dynamics model 440 which receives as input, a physiological signal. The physiological signal may be a waveform corresponding to a user desired frequency, duration, and/or amplitude associated with a physiological characteristic. For example, the physiological signal 436 may correspond to a heart rate and may be provided as a heartrate waveform including systole, diastole, and dicrotic notch portions. In some examples, the heartrate waveform may include a P wave, which represents the depolarization of the atria; the QRS complex, which represents the depolarization of the ventricles; and the T wave, which represents the repolarization of the ventricles. Alternatively, or in addition, the physiological signal may correspond to a respiratory waveform, a blushing waveform, and/or a blinking waveform. Although specific waveforms have been identified, it should be understood that any physiological characteristic that maybe triggered in some fashion and/or duration may be provided as the physiological signal 436 and superimposed on an input image 408 and/or the frames and/or images of an input video 404. In addition, as the physiological signal 436 may vary with time, a value of the physiological signal may different for successive frames of video. The physiological signal 436 may be dependent on or otherwise based on a frame of video.

In some instances, external factors 430 may modify one or more of the spatial distribution model 412 (spatial distribution model), the color space model 432, and the temporal dynamics model 440. For example, where the external factor is a temperature characteristic—such as a cold environment—one or more external factors may cause one or more of the machine learning model 412 (spatial distribution model), the color space model 432, and the temporal dynamics model 440 to output a different weighting, or coefficient, to more truly reflect a cold environment. For instance, in a cold environment, a pulse may be slower, less blood may flow, and/or skin tones may change. Similarly, where an avatar is in a warm environment and/or undergoing physical activity, more blood may flow impacting skin color in one or more locations provided by an attention mask, such as the attention mask 424. Further, a heart rate and/or respiratory rate may increase further impacting the attention mask 424, color channel coefficients 438, and/or the physiological signal 444. In some examples, a position of the avatar (e.g., upside down) may impact blood flow and pooling and may be accounted for with an external factor 430. Further, the external factor may reflect an emotional state of the avatar (e.g., happy, sad, excited, scared); such may cause one or more of the machine learning model 412 (spatial distribution model), the color space model 432, and the temporal dynamics model 440 to output a different weighting, or coefficient, to more truly reflect the state of the avatar.

As further depicted in FIG. 4, a physiological mask overlay 428 may be generated for each color channel. The physiological mask overlay 428 may represent one or more coefficients and/or weighting factors that are to be adjusted per pixel location (e.g., x,y location in the input image 108). For example, a red color channel for a pixel located at coordinates x,y and a time t, may be calculated as follows:

$$R'_{xyt}=R_{xyt}+\gamma*0.23*M_{xy}*BVP_t$$

where $R_{xyt}$ is the original red pixel value, γ is a user supplied tuning parameter, 0.23 is a color channel coefficient provided by the color space model, $M_{xy}$ corresponds to an attention weight from the attention mask 424 to be applied to the pixel location, $BVP_t$ corresponds to a physiological signal, such as a blood volume pulse at time=t, and $R'_{xyt}$ is the resulting pixel value for the pixel location at x,y, and time equal to t. A pixel adjustment value may be equal to the product of the tuning parameter γ, the color channel coefficient provided by the color space model, the attention weight $M_{xy}$ from the attention mask 424 to be applied to the pixel location, and the physiological signal $BVP_t$. The pixel adjustment value may be applied to the exiting pixel to generate the augmented pixel. The blue color channel pixels and the green color pixel channels are determined in the same or similar manner. The physiological overlay is then applied to the input frame and the three resulting color masks 446, or alpha masks, are combined to form the output image 448. The coefficients (0.23, 0.41, 0.36) depicted in FIG. 4 are based on the hemoglobin absorption profile; as such, the coefficients (e.g., the numbers) may be different depending on the lighting conditions in the image/video. That is, the channel color coefficients 438 are a function of the hemoglobin absorption profile, the blood oxygen content and the lighting (inferred from the pixel information in the input image 408 (*xt*). In some examples, color masks other than RGB may be used. For example, color masks including luminance and chrominance channels (e.g., YUV, Y'UV, YCrCb, Y'CrCb may be used. Similarly, color masks based on hue, saturation, and value (HSV) may be used. The output image 448 is an image having the physiological characteristic superimposed or otherwise applied based on a provided physiological signal and input video. Accordingly, each frame and/or image in the input video 404 may be augmented in a similar manner and the augmented frames may be grouped into a video sequence. Although described as including an input video 404, in some examples a single image may be augmented to add additional detail to the image. For example, where the image includes a cold environment, the image may be augmented to depict an avatar, or other subject within the image, in the cold environment. That is, skin tone and coloration may modified based on the temperature of the environment. Similarly, where one desires to augment an avatar, or other subject within the image, with an emotional state, emotion, or other external factor, such input image may be processed as described with respect to FIG. 4, where an augmented image, rather than video, is output.

In some examples, a vector, such as a motion vector, may account for pixel dynamics such as pixel movement and pixel translation. For example, a region, portion, or area represented by one or more pixels, may move from a first location in a first frame to a second location in a second frame. Accordingly, the vector may provide a mechanism for identifying and/or addressing specific pixels of the input image that move or translate when applying the physiological characteristic to the input image. As an example, blood flowing through a vein, artery, and/or under the skin may cause the vein, artery, and/or skin to distort in one or more directions. The vector may account for such movement, or translation, between frames.

The vector may be identified utilizing an attention mask or other mask that provides a mechanism for identifying and/or addressing specific pixels of the input image 408 that are to be modified when applying the physiological characteristic to the input image. The mask may be based on features extracted by or otherwise identified by the machine learning model 412 based on the input image 408, where such features are identified as areas of or portions of the input image 408 that are to be modified by the physiological characteristic. In examples, the physiological characteristic may be one or more of a blood volume pulse, blushing, blinking, and/or breathing. The mask may indicate a direction and magnitude corresponding to a pixel in skin areas with stronger signals, such as those skin areas of the face that are to be augmented with the physiologic characteristic. Each vector in the mask may correspond to a pixel of the input image 408 and may be considered as a pixel adjustment value. Further, the attention mask may vary with each frame of video.

Figure 5:
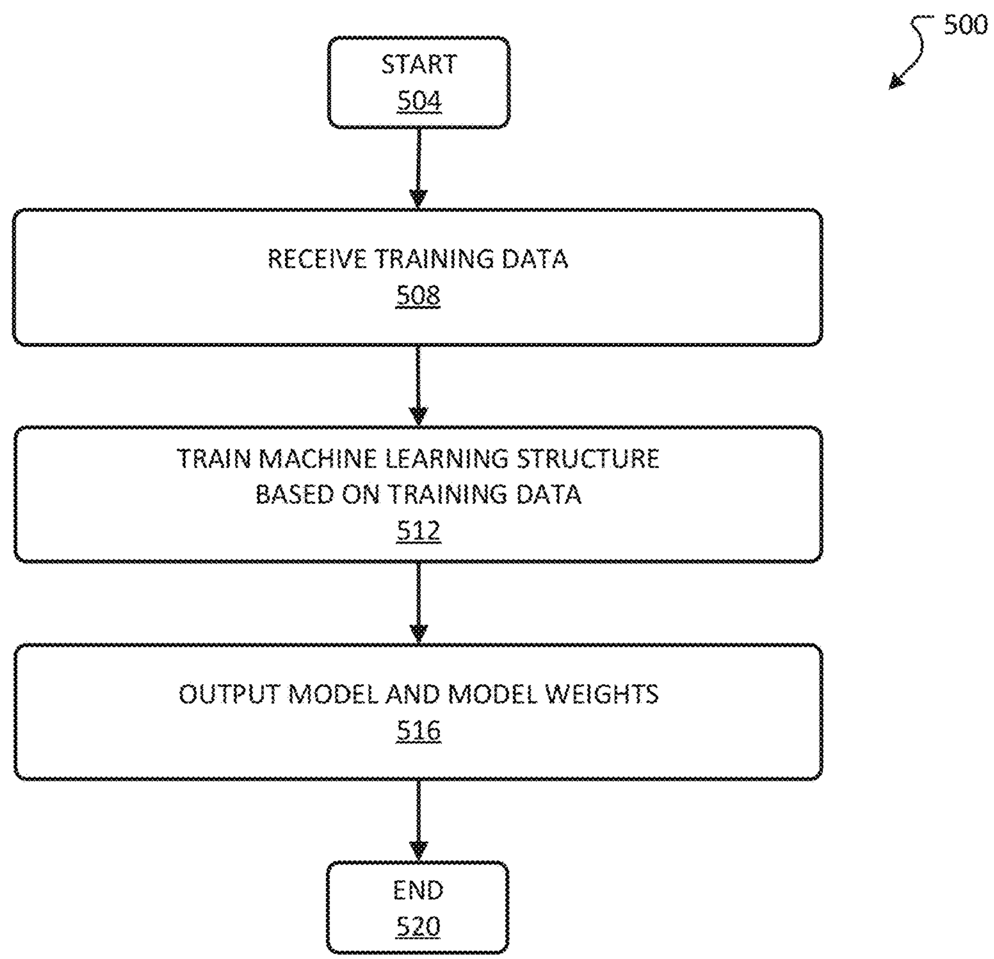
FIG. 5 depicts a method directed to training a machine learning model in accordance with examples of the present disclosure.

FIG. 5 depicts details of a method 500 for training a machine learning structure in accordance with examples of the present disclosure. A general order for the steps of the method 500 is shown in FIG. 5. Generally, the method 500 starts at 504 and ends at 520. The method 500 may include more or fewer steps or may arrange the order of the steps differently than those shown in FIG. 5. The method 500 can be executed as a set of computer-executable instructions executed by a computer system and encoded or stored on a computer readable medium. Further, the method 500 can be performed by gates or circuits associated with a processor, Application Specific Integrated Circuit (ASIC), a field programmable gate array (FPGA), a system on chip (SOC), or other hardware device. Hereinafter, the method 500 shall be explained with reference to the systems, components, modules, software, data structures, user interfaces, etc. described in conjunction with FIGS. 1-4.

The method starts at 504, where flow may proceed to 508. At 508, training data may be received. The training data may correspond to the training data 204 and may include video segments utilized to train the machine learning structure to accurately detected or predict an attention mask based on a physiological input signal and a plurality of input frames or images from a video segment Once the training data has been received at 508, the method may proceed to 512 where the machine learning structure may be trained based on the training data. For example, the machine learning structure may include two paths as discussed with respect to FIG. 3. A first path may be associated with a motion model and a second path associated with an appearance model. The architecture of the motion model may include various layers and hidden units and may include an average pooling and hyperbolic tangent that may be utilized as an activation function. The architecture of the appearance model may be the same as or similar to the motion model. In addition to a one-dimensional physiological signal such as blood volume pulse, the machine learning structure may output an attention mask, such as the attention mask 328/332 for each video frame of a video segment. The attention mask indicates which portion or regions of the input image were used to compute the recovered physiological signal, such as the blood volume pulse.

The motion model allows the machine learning structure to differentiate between intensity variations caused by noise, e.g., from motion from subtle characteristic intensity variations induced by the physiological characteristic. The motion representation is computed from the input difference of two consecutive video frames (e.g., C(t) and C(t+1). The appearance model allows the machine learning structure to learn which regions in the image are likely to be reliable for computing strong physiological signals, such as iPPG signals. The appearance model may generate a representation from each input video frame's texture and color information. The appearance model guides the motion representation to recover iPPG signals from various regions included in the input image, and to further differentiate between them from other sources of noise. The appearance model may take as input a single image or frame of video.

The recovered physiological signal may be compared to the training physiological signal and may be validated with test data. Once a satisfactory amount of error is achieved, the machine learning structure may be output as a machine learning model at 516, where the structure of the machine learning model may be stored in the model file and the various weights of the machine learning model are stored in a location associated with a weight file. Once the model has been generated, the method 500 may end at 520.

Figure 6:
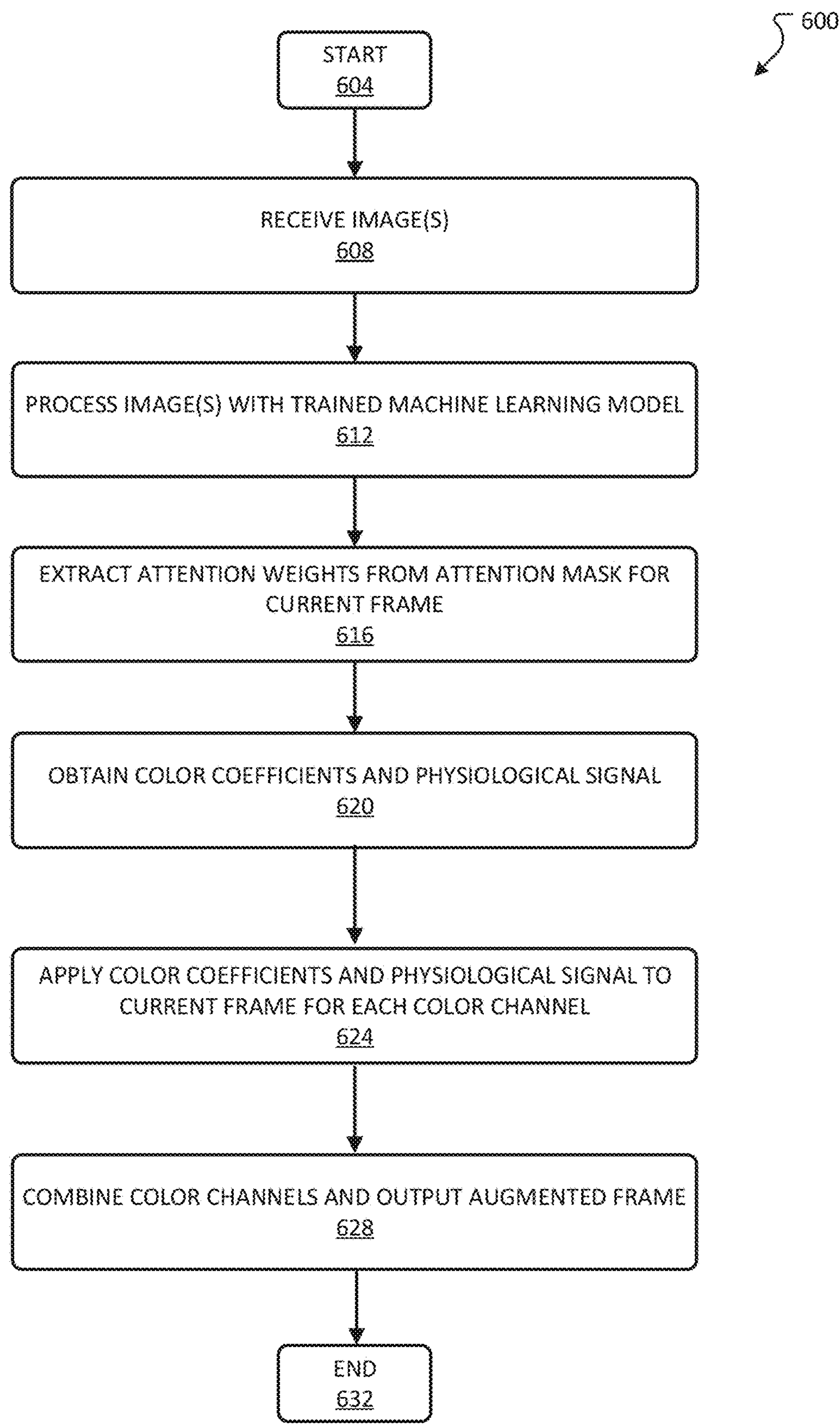
FIG. 6 depicts a method directed applying a physiologic characteristic to a video sequence in accordance with examples of the present disclosure.

FIG. 6 depicts details of a method 600 for superimposing or otherwise applying a physiological signal to a video segment in accordance with examples of the present disclosure. A general order for the steps of the method 600 is shown in FIG. 6. Generally, the method 600 starts at 604 and ends at 632. The method 600 may include more or fewer steps or may arrange the order of the steps differently than those shown in FIG. 6. The method 600 can be executed as a set of computer-executable instructions executed by a computer system and encoded or stored on a computer readable medium. Further, the method 600 can be performed by gates or circuits associated with a processor, Application Specific Integrated Circuit (ASIC), a field programmable gate array (FPGA), a system on chip (SOC), or other hardware device. Hereinafter, the method 600 shall be explained with reference to the systems, components, modules, software, data structures, user interfaces, etc. described in conjunction with FIGS. 1-5.

The method starts at 604, where flow may proceed to 608. At 608, a video segment including a plurality of images may be received. Such received images may correspond to images in a video segment that are to be modified based on the application of a physiological signal, such as a physiological signal 436 for example. The method 600 may proceed to 612, where the video frames or images, may be provided to the trained model. The input frame, or image, may be processed, such as according to the motion model 320. That is, a machine learning model, also referred to as a spatial distribution model, may utilize the machine learning model to obtain an attention mask that includes at least one weight or scaler for each pixel in the input frame or input image. As previously discussed, the attention mask may correspond to a mask having a same or similar dimension to that of the input image. The attention mask may provide a mechanism for identifying and/or addressing specific pixels of the input image that are to be modified when applying the physiological characteristic to the input image. The attention mask may be based on features extracted by or otherwise identified by the machine learning model based on the input image, where such features are identified as areas of or portions of the input image that are to be modified by the physiological characteristic. In examples, the physiological characteristic may be one or more of a blood volume pulse, blushing, blinking, and/or breathing. The attention mask may assign higher weights to skin areas with stronger signals, such as those skin areas of the face that are to be augmented with the physiologic characteristic. The attention mask may identify areas of a user's face within an image or frame of video in which to apply the physiological signal. Each weight or weighting for each pixel in the attention mask may correspond to a pixel of the input image and may be extracted at 616.

The method may then proceed to 620, where the color coefficients and physiological signal may be obtained. For example, a color space model may determine color channel coefficients to apply to each pixel of the input image. In some instances, the color channel coefficients are preprogramed or otherwise included in the color space model; in some instances, the color channel coefficients may be provided as an external input, such as the color channel coefficients. In some instances, the color channel coefficients may be adjusted or modified based on user and/or machine learning model preference. In addition to the color space model and the spatial distribution model, also referred to as the machine learning model, the computing device may execute a temporal dynamics model which receives as input, a physiological signal. The physiological signal may be a waveform corresponding to a user desired frequency, duration, and/or amplitude associated with a physiological characteristic. For example, the physiological signal may correspond to a heart rate and may be provided as a heartrate waveform including systole, diastole, and dicrotic notch portions. Alternatively, or in addition, the physiological signal may correspond to a respiratory waveform, a blushing waveform, and/or a blinking waveform. Although specific waveforms have been identified, it should be understood that any physiological characteristic that maybe triggered in some fashion and/or duration may be provided as the physiological signal and superimposed on an input image and/or the frames and/or images of an input video.

At 624, the method 600 may apply the color coefficients and physiological signal to the current frame for each color channel based on the attention weights. For example, a physiological mask overlay may be generated for each color channel, where the physiological mask overlay represents one or more coefficients and/or weighting factors that are to be adjusted per pixel location (e.g., x,y location in the input image). In some examples, a color mask, or alpha mask may be generated for each color channel with appropriate attention weights, color coefficients, and temporal augmentation based on the physiologic input signal. The color channels may then be combined, and an augmented frame or image may be provided as an output at 628. Method 600 may end at 632.

Figure 7:
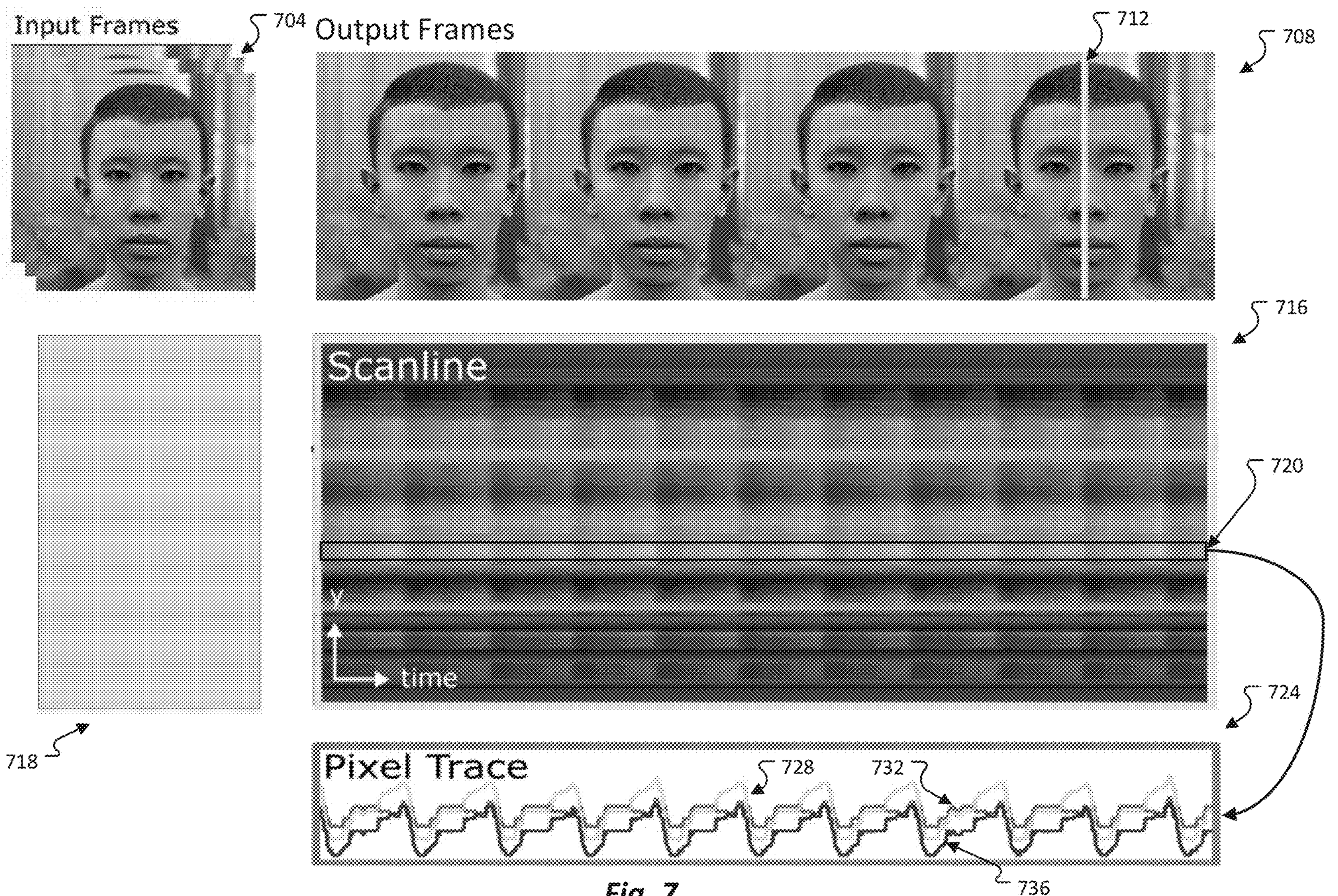
FIG. 7 depicts example output frames including a physiologic characteristic in accordance with examples of the present disclosure.

FIG. 7 depicts an example application directed to applying a blood volume pulse physiological signal to a series of input frames 704 in accordance with examples of the present disclosure. More specifically, the input frames 704 may include a plurality of images; the plurality of images may be input to the computing device 402 for example together with a blood volume pulse signal. The computing device 402 may provide a series of output frames 708 augmented with a blood volume pulse signal. A scanline 712 is temporally represented on the graph 716. Over time, the scanline may change depending on which output frame is analyzed, as depicted by 720. In addition, the graph 716 depicts a change in pixel color over time. The change in pixel color may also be shown in the pixel trace 724. For example, the pixel trace 724 generally identifies a red channel 736, a green channel 728, and a blue channel 732. The peak of the pixel trace corresponds to an augmented image and/or image pixel. For example, where the input frame or input images depict an avatar, the physiological information of the avatar may be nonexistent, as depicted in the exaggerated scanline 718. However, upon applying the blood volume pulse to the avatar in the input frame 704, the graph 716 depicts peak intensities or colors, indicating that the blood volume pulse has been applied. Accordingly, the avatar in output frames 708 may appear more friendly and trustworthy.

Figure 8:
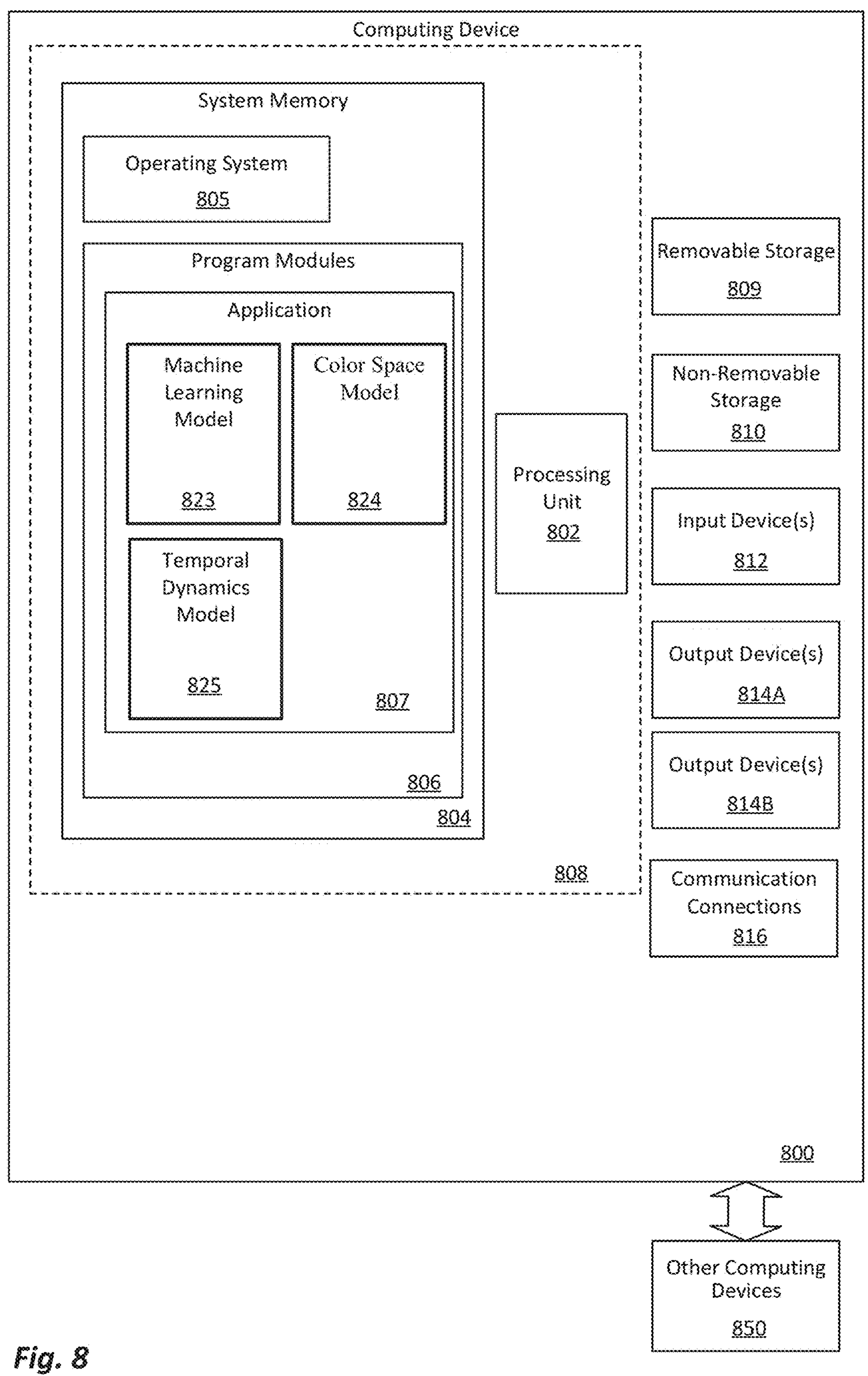
FIG. 8 depicts block diagram illustrating physical components (e.g., hardware) of a computing device with which aspects of the disclosure may be practiced.
Figure 9A:
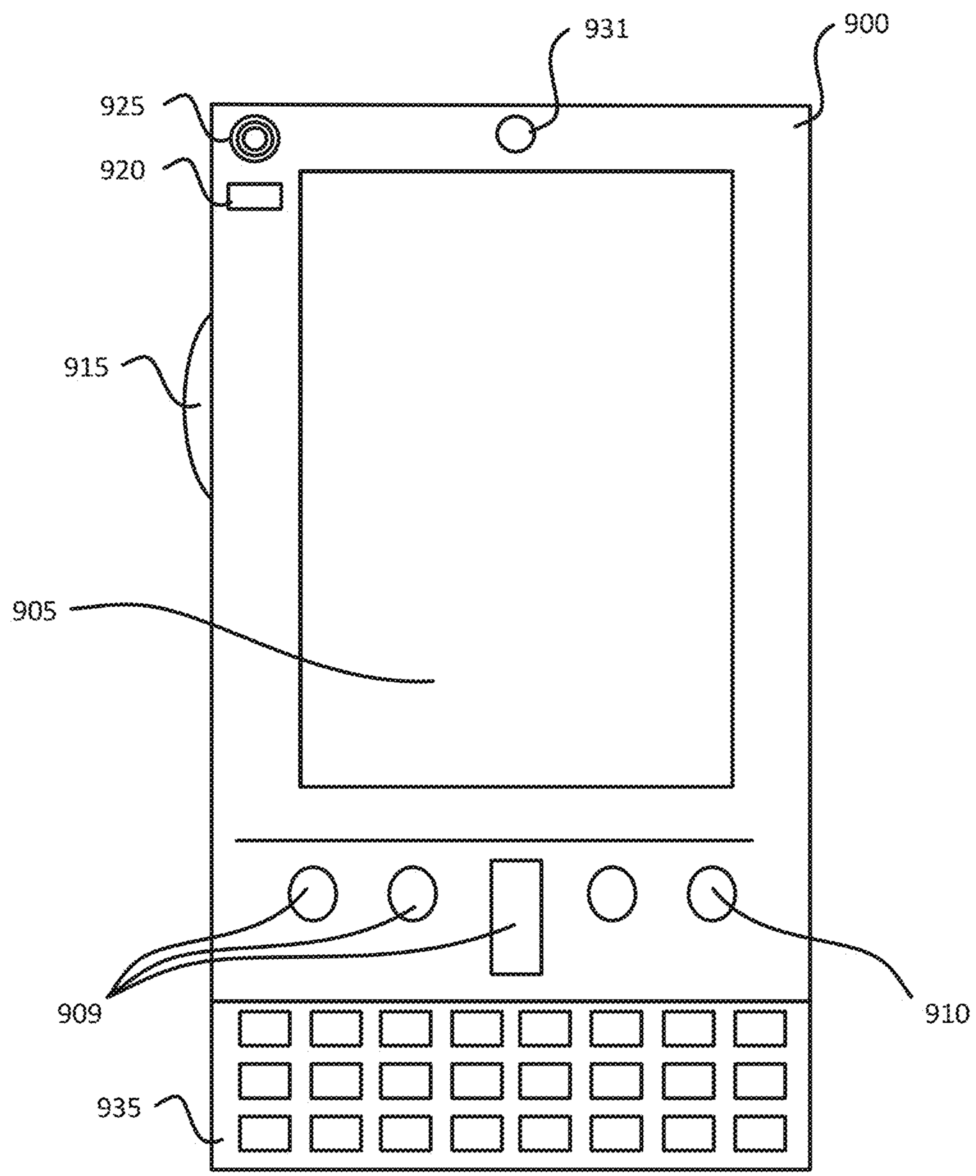
FIG. 9A illustrates a first example of a computing device with which aspects of the disclosure may be practiced.
Figure 9B:
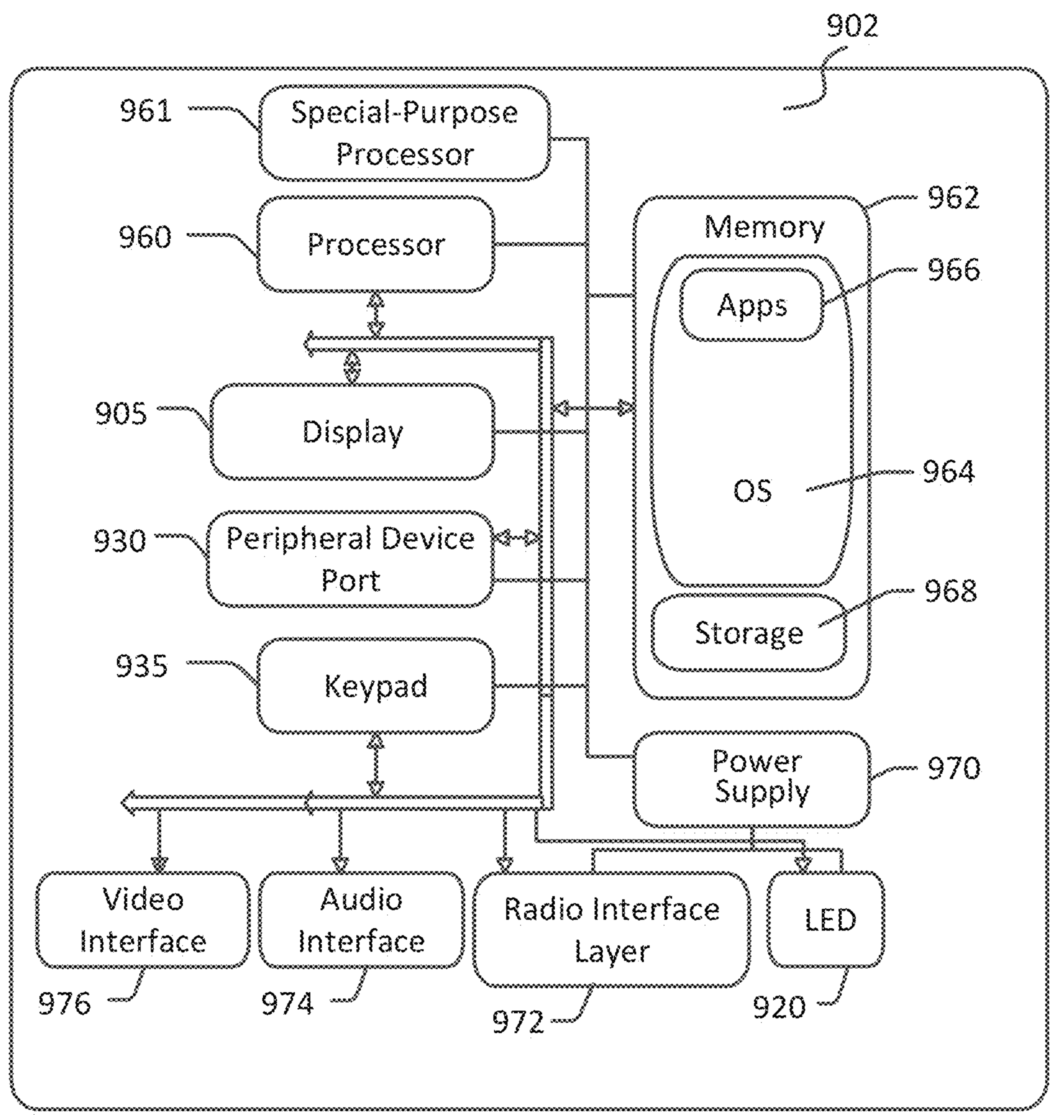
FIG. 9B illustrates a second example of a computing device with which aspects of the disclosure may be practiced.
Figure 10:
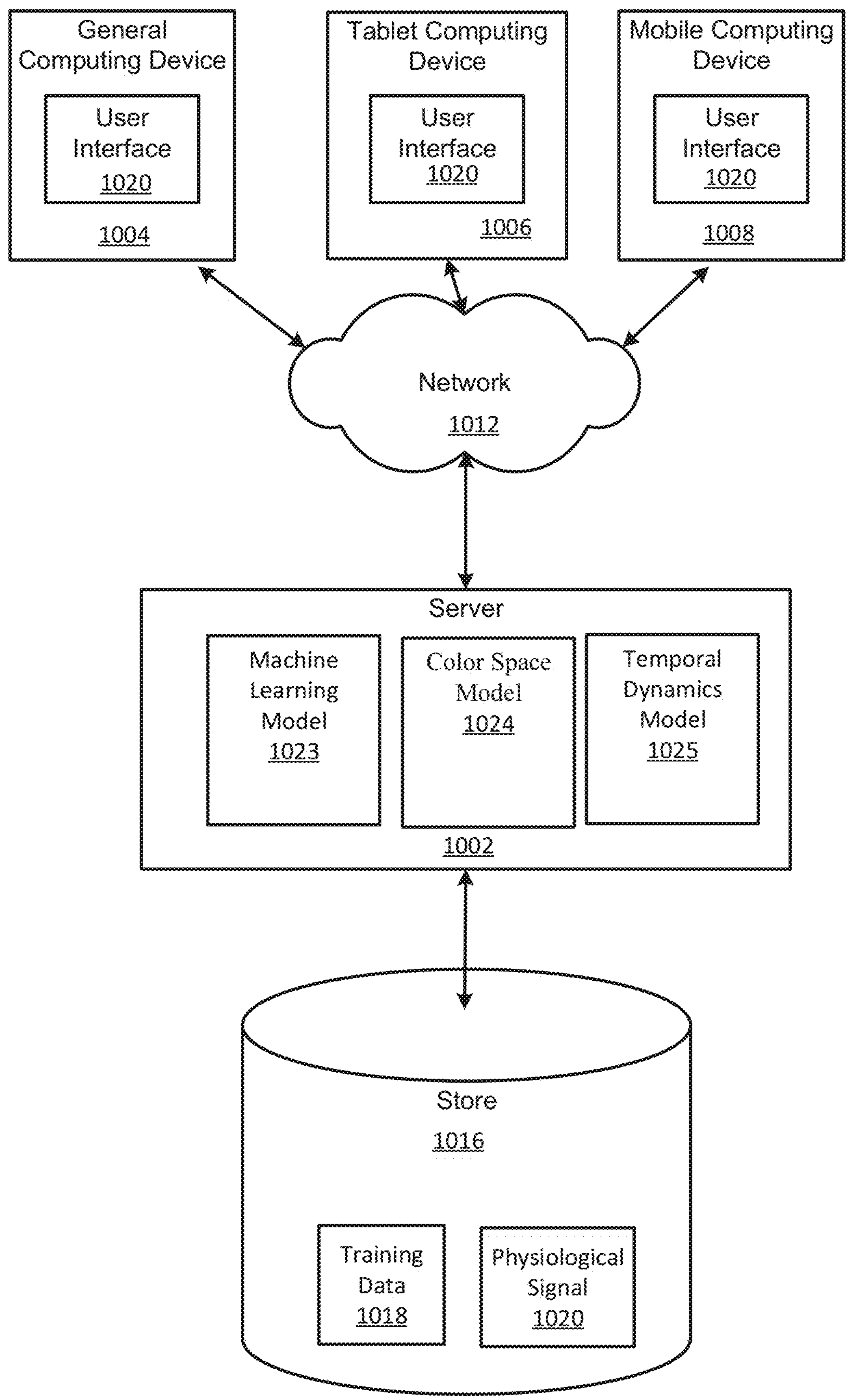
FIG. 10 illustrates at least one aspect of an architecture of a system for processing data in accordance with examples of the present disclosure.

FIGS. 8-10 and the associated descriptions provide a discussion of a variety of operating environments in which aspects of the disclosure may be practiced. However, the devices and systems illustrated and discussed with respect to FIGS. 8-10 are for purposes of example and illustration and are not limiting of a vast number of computing device configurations that may be utilized for practicing aspects of the disclosure, described herein.

FIG. 8 is a block diagram illustrating physical components (e.g., hardware) of a computing device 800 with which aspects of the disclosure may be practiced. The computing device components described below may be suitable for the computing devices described above. In a basic configuration, the computing device 800 may include at least one processing unit 802 and a system memory 804. Depending on the configuration and type of computing device, the system memory 804 may comprise, but is not limited to, volatile storage (e.g., random access memory), non-volatile storage (e.g., read-only memory), flash memory, or any combination of such memories.

The system memory 804 may include an operating system 805 and one or more program modules 806 suitable for running software applications 807, such as but not limited to a machine learning model 823 and a temporal dynamics model 825. The machine learning model 823 may be the same as or similar to the machine learning models 120, 244, 344, and 412 as described with respect to, but not limited to, at least FIGS. 1-7 of the present disclosure. The color space model 824 may be the same as or similar to the color space model 432 as described with respect to, but not limited to, at least FIGS. 1-7 of the present disclosure. The temporal dynamics model 825 may be the same as or similar to the temporal dynamics model 440 as described with respect to, but not limited to, at least FIGS. 1-7 of the present disclosure. The operating system 805, for example, may be suitable for controlling the operation of the computing device 800.

Furthermore, embodiments of the disclosure may be practiced in conjunction with a graphics library, other operating systems, or any other application program and is not limited to any particular application or system. This basic configuration is illustrated in FIG. 8 by those components within a dashed line 808. The computing device 800 may have additional features or functionality. For example, the computing device 800 may also include additional data storage devices (removable and/or non-removable) such as, for example, magnetic disks, optical disks, or tape. Such additional storage is illustrated in FIG. 8 by a removable storage device 809 and a non-removable storage device 810.

As stated above, several program modules and data files may be stored in the system memory 804. While executing on the at least one processing unit 802, the program modules 806 may perform processes including, but not limited to, one or more aspects, as described herein. Other program modules that may be used in accordance with aspects of the present disclosure may include electronic mail and contacts applications, word processing applications, spreadsheet applications, database applications, slide presentation applications, drawing or computer-aided application programs, etc., and/or one or more components supported by the systems described herein.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 8 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, with respect to the capability of client to switch protocols may be operated via application-specific logic integrated with other components of the computing device 800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

The computing device 800 may also have one or more input device(s) 812 such as a keyboard, a mouse, a pen, a sound or voice input device, a touch or swipe input device, etc. The output device(s) 814A such as a display, speakers, a printer, etc. may also be included. An output 814B, corresponding to a virtual display may also be included. The aforementioned devices are examples and others may be used. The computing device 800 may include one or more communication connections 816 allowing communications with other computing devices 850. Examples of suitable communication connections 816 include, but are not limited to, radio frequency (RF) transmitter, receiver, and/or transceiver circuitry; universal serial bus (USB), parallel, and/or serial ports.

The term computer readable media as used herein may include computer storage media. Computer storage media may include volatile and nonvolatile, removable and non-removable media implemented in any method or technology for storage of information, such as computer readable instructions, data structures, or program modules. The system memory 804, the removable storage device 809, and the non-removable storage device 810 are all computer storage media examples (e.g., memory storage). Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 800. Any such computer storage media may be part of the computing device 800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term “modulated data signal” may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

FIGS. 9A and 9B illustrate a computing device or mobile computing device 900, for example, a mobile telephone, a smart phone, wearable computer (such as a smart watch), a tablet computer, a laptop computer, and the like, with which aspects of the disclosure may be practiced. With reference to FIG. 9A, one aspect of a mobile computing device 900 for implementing the aspects is illustrated. In a basic configuration, the mobile computing device 900 is a handheld computer having both input elements and output elements. The mobile computing device 900 typically includes a display 905 and one or more input buttons 909/910 that allow the user to enter information into the mobile computing device 900. The display 905 of the mobile computing device 900 may also function as an input device (e.g., a touch screen display). If included, an optional side input element 915 allows further user input. The side input element 915 may be a rotary switch, a button, or any other type of manual input element. In alternative aspects, mobile computing device 900 may incorporate more or less input elements. For example, the display 905 may not be a touch screen in some aspects. In yet another alternative aspect, the mobile computing device 900 is a portable phone system, such as a cellular phone. The mobile computing device 900 may also include an optional keypad 935. Optional keypad 935 may be a physical keypad or a “soft” keypad generated on the touch screen display. In various aspects, the output elements include the display 905 for showing a graphical user interface (GUI), a visual indicator 931 (e.g., a light emitting diode), and/or an audio transducer 925 (e.g., a speaker). In some aspects, the mobile computing device 900 incorporates a vibration transducer for providing the user with tactile feedback. In yet another aspect, the mobile computing device 900 incorporates input and/or output ports 930, such as an audio input (e.g., a microphone jack), an audio output (e.g., a headphone jack), and a video output (e.g., a HDMI port) for sending signals to or receiving signals from an external source.

FIG. 9B is a block diagram illustrating the architecture of one aspect of computing device, a server, or a mobile computing device. That is, the mobile computing device 900 can incorporate a system (902) (e.g., an architecture) to implement some aspects. The system 902 can implemented as a “smart phone” capable of running one or more applications (e.g., browser, e-mail, calendaring, contact managers, messaging clients, games, and media clients/players). In some aspects, the system 902 is integrated as a computing device, such as an integrated personal digital assistant (PDA) and wireless phone.

One or more application programs 966 may be loaded into the memory 962 and run on or in association with the operating system 964. Examples of the application programs include phone dialer programs, e-mail programs, personal information management (PIM) programs, word processing programs, spreadsheet programs, Internet browser programs, messaging programs, and/or one or more components supported by the systems described herein. The system 902 also includes a non-volatile storage area 968 within the memory 962. The non-volatile storage area 968 may be used to store persistent information that should not be lost if the system 902 is powered down. The application programs 966 may use and store information in the non-volatile storage area 968, such as e-mail or other messages used by an e-mail application, and the like. A synchronization application (not shown) also resides on the system 902 and is programmed to interact with a corresponding synchronization application resident on a host computer to keep the information stored in the non-volatile storage area 968 synchronized with corresponding information stored at the host computer. As should be appreciated, other applications may be loaded into the memory 962 and run on the mobile computing device 900 described herein (e.g. a machine learning model 823 and a temporal dynamics model 825, etc.).

The system 902 has a power supply 970, which may be implemented as one or more batteries. The power supply 970 might further include an external power source, such as an AC adapter or a powered docking cradle that supplements or recharges the batteries.

The system 902 may also include a radio interface layer 972 that performs the function of transmitting and receiving radio frequency communications. The radio interface layer

972 facilitates wireless connectivity between the system 902 and the "outside world," via a communications carrier or service provider. Transmissions to and from the radio interface layer 972 are conducted under control of the operating system 964. In other words, communications received by the radio interface layer 972 may be disseminated to the application programs 966 via the operating system 964, and vice versa.

The visual indicator 920 may be used to provide visual notifications, and/or an audio interface 974 may be used for producing audible notifications via the audio transducer 925. In the illustrated configuration, the visual indicator 920 is a light emitting diode (LED) and the audio transducer 925 is a speaker. These devices may be directly coupled to the power supply 970 so that when activated, they remain on for a duration dictated by the notification mechanism even though the processor 960/961 and other components might shut down for conserving battery power. The LED may be programmed to remain on indefinitely until the user takes action to indicate the powered-on status of the device. The audio interface 974 is used to provide audible signals to and receive audible signals from the user. For example, in addition to being coupled to the audio transducer 925, the audio interface 974 may also be coupled to a microphone to receive audible input, such as to facilitate a telephone conversation. In accordance with aspects of the present disclosure, the microphone may also serve as an audio sensor to facilitate control of notifications, as will be described below. The system 902 may further include a video interface 976 that enables an operation of an on-board camera to record still images, video stream, and the like.

A mobile computing device 900 implementing the system 902 may have additional features or functionality. For example, the mobile computing device 900 may also include additional data storage devices (removable and/or non-removable) such as, magnetic disks, optical disks, or tape. Such additional storage is illustrated in FIG. 9B by the non-volatile storage area 968.

Data/information generated or captured by the mobile computing device 900 and stored via the system 902 may be stored locally on the mobile computing device 900, as described above, or the data may be stored on any number of storage media that may be accessed by the device via the radio interface layer 972 or via a wired connection between the mobile computing device 900 and a separate computing device associated with the mobile computing device 900, for example, a server computer in a distributed computing network, such as the Internet. As should be appreciated such data/information may be accessed via the mobile computing device 900 via the radio interface layer 972 or via a distributed computing network. Similarly, such data/information may be readily transferred between computing devices for storage and use according to well-known data/information transfer and storage means, including electronic mail and collaborative data/information sharing systems.

FIG. 10 illustrates one aspect of the architecture of a system for processing data received at a computing system from a remote source, such as a personal computer 1004, tablet computing device 1006, or mobile computing device 1008, as described above. Content displayed at server device 1002 may be stored in different communication channels or other storage types.

In some aspects, one or more of a machine learning model 1023, a color space model 1024, and a temporal dynamics model 1025, may be employed by server device 1002. The server device 1002 may provide data to and from a client computing device such as a personal computer 1004, a tablet computing device 1006 and/or a mobile computing device 1008 (e.g., a smart phone) through a network 1012. By way of example, the computer system described above may be embodied in a personal computer 1004, a tablet computing device 1006 and/or a mobile computing device 1008 (e.g., a smart phone). Any of these embodiments of the computing devices may obtain content from the store 1016, in addition to receiving graphical data useable to be either pre-processed at a graphic-originating system, or post-processed at a receiving computing system. The content store may include training data 1018 and physiological signals 1020.

FIG. 10 illustrates an exemplary mobile computing device 1008 that may execute one or more aspects disclosed herein. In addition, the aspects and functionalities described herein may operate over distributed systems (e.g., cloud-based computing systems), where application functionality, memory, data storage and retrieval and various processing functions may be operated remotely from each other over a distributed computing network, such as the Internet or an intranet. User interfaces and information of various types may be displayed via on-board computing device displays or via remote display units associated with one or more computing devices. For example, user interfaces and information of various types may be displayed and interacted with on a wall surface onto which user interfaces and information of various types are projected. Interaction with the multitude of computing systems with which embodiments of the invention may be practiced include, keystroke entry, touch screen entry, voice or other audio entry, gesture entry where an associated computing device is equipped with detection (e.g., camera) functionality for capturing and interpreting user gestures for controlling the functionality of the computing device, and the like.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Any of the steps, functions, and operations discussed herein can be performed continuously and automatically.

The exemplary systems and methods of this disclosure have been described in relation to computing devices. However, to avoid unnecessarily obscuring the present disclosure, the preceding description omits several known structures and devices. This omission is not to be construed as a limitation. Specific details are set forth to provide an understanding of the present disclosure. It should, however, be appreciated that the present disclosure may be practiced in a variety of ways beyond the specific detail set forth herein.

Furthermore, while the exemplary aspects illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infrared data communications.

While the flowcharts have been discussed and illustrated in relation to a particular sequence of events, it should be appreciated that changes, additions, and omissions to this sequence can occur without materially affecting the operation of the disclosed configurations and aspects.

Several variations and modifications of the disclosure can be used. It would be possible to provide for some features of the disclosure without providing others.

In yet another configurations, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another configuration, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another configuration, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

The disclosure is not limited to standards and protocols if described. Other similar standards and protocols not mentioned herein are in existence and are included in the present disclosure. Moreover, the standards and protocols mentioned herein, and other similar standards and protocols not mentioned herein are periodically superseded by faster or more effective equivalents having essentially the same functions. Such replacement standards and protocols having the same functions are considered equivalents included in the present disclosure.

In accordance with at least one example of the present disclosure, a method for applying a physiological characteristic to a portion of video is provided. The method may include receiving a frame of a video sequence, receiving a physiological signal, generating an attention mask based on the received physiological signal, wherein the attention mask includes attention weights indicative of a strength of the physiological signal for differing portions of the frame of the video sequence, generating a pixel adjustment value based on the physiological signal and the attention mask, and applying the pixel adjustment value to an identified pixel in the frame of the video sequence.

In accordance with at least one aspect of the above method, the method may include generating a second pixel adjustment value based on the physiological signal and the attention mask, the second pixel adjustment value being different from the pixel adjustment value, and applying the second pixel adjustment value to a second identified pixel in the frame of the video sequence, wherein the second identified pixel is different from the identified pixel. In accordance with at least one aspect of the above method, the method may include where the attention mask identifies areas of an avatar depicted in the video sequence that are affected by the physiological signal. In accordance with at least one aspect of the above method, the method may include where the attention mask is generated from a machine learning model specifically trained to generate attention masks based on a frame of a video sequence and the physiological signal. In accordance with at least one aspect of the above method, the method may include where the physiological signal is at least one of a blood volume pulse rate, a blinking rate, or a respiratory rate. In accordance with at least one aspect of the above method, the method may include generating another pixel adjustment value based on the physiological signal, the attention mask, and color coefficients, wherein the color coefficients are specific to the physiological characteristic. In accordance with at least one aspect of the above method, the method may include where applying the color coefficients includes generating an alpha mask for each color of the color coefficients and combining the alpha masks to obtain an output frame. In accordance with at least one aspect of the above method, the method may include where the pixel adjustment value is vector corresponding to a direction and magnitude for one or more pixels.

In accordance with at least one example of the present disclosure, a computer-readable media including instructions is provided. When the instructions are executed by a processor, the instructions cause the processor to receive a frame of a video sequence, receive a physiological signal, generate an attention mask based on the received physiological signal, wherein the attention mask includes attention weights indicative of a strength of the physiological signal for differing portions of the frame of the video sequence, generate an alpha mask for a first color based on the frame of the video sequence, the physiological signal, the attention mask, and a color channel coefficient associated with the first color, and combine the generated alpha mask for the first color with an alpha mask of a second color to generate an output frame.

In accordance with at least one aspect of the above computer-readable media, the attention mask identifies areas of an avatar depicted in the video sequence that are affected by the physiological signal. In accordance with at least one aspect of the above computer-readable media, the physiological signal is at least one of a blood volume pulse rate, a blinking rate, or a respiratory rate. In accordance with at least one aspect of the above computer-readable media, the attention mask is generated from a machine learning model specifically trained to generate attention masks based on a frame of a video sequence and the physiological signal. In accordance with at least one aspect of the above computer-readable media, the instructions may cause the processor to receive an external factor affecting at least one of the color coefficients, attention mask, or physiological signal.

In accordance with at least one example of the present disclosure, a system for applying a physiological characteristic to a portion of video is provided. The system may include a processor and memory storing instructions, which when executed by the processor, cause the processor to receive a frame of a video sequence, receive a physiological signal, generate an attention mask based on the received physiological signal, wherein the attention mask includes attention weights indicative of a strength of the physiological signal for differing portions of the frame of the video sequence, generate a pixel adjustment value based on the physiological signal and the attention mask, and apply the pixel adjustment value to an identified pixel in the frame of the video sequence.

In accordance with at least one aspect of the above system, the instructions cause the processor to generate a second pixel adjustment value based on the physiological signal and the attention mask, the second pixel adjustment value being different from the pixel adjustment value, apply the second pixel adjustment value to a second identified pixel in the frame of the video sequence, wherein the second identified pixel is different from the identified pixel. In accordance with at least one aspect of the above system, the attention mask identifies areas of an avatar depicted in the video sequence that are affected by the physiological signal. In accordance with at least one aspect of the above system, the attention mask is generated from a machine learning model specifically trained to generate attention masks based on a frame of a video sequence and the physiological signal. In accordance with at least one aspect of the above system, the instructions cause the processor to generate another pixel adjustment value based on the physiological signal, the attention mask, and color coefficients, wherein the color coefficients are specific to the physiological characteristic. In accordance with at least one aspect of the above system, applying the color coefficients includes generating an alpha mask for each color of the color coefficients and combining the alpha masks to obtain an output frame. In accordance with at least one aspect of the above system, the instructions cause the processor to receive an external factor affecting at least one of the color coefficients, attention mask, or physiological signal, and generate the another pixel adjustment value based on the external factor.

The present disclosure, in various configurations and aspects, includes components, methods, processes, systems and/or apparatus substantially as depicted and described herein, including various combinations, subcombinations, and subsets thereof. Those of skill in the art will understand how to make and use the systems and methods disclosed herein after understanding the present disclosure. The present disclosure, in various configurations and aspects, includes providing devices and processes in the absence of items not depicted and/or described herein or in various configurations or aspects hereof, including in the absence of such items as may have been used in previous devices or processes, e.g., for improving performance, achieving ease, and/or reducing cost of implementation.

The invention claimed is:

1. A method for applying a physiological characteristic to a portion of video, the method comprising:
- receiving a physiological signal;
- generating an attention mask based on the received physiological signal;
- generating a pixel adjustment value based on the physiological signal and the attention mask; and
- applying the pixel adjustment value to a pixel in a texture of an avatar.

2. The method of claim 1, wherein:
- the pixel adjustment value is a first pixel adjustment value;
- the pixel is a first pixel; and
- the method further comprises:
  - generating a second pixel adjustment value based on the physiological signal and the attention mask, wherein the second pixel adjustment value is different than the first pixel adjustment value; and
  - applying the second pixel adjustment value to a second pixel in the texture of the avatar, wherein the second identified pixel is different than the first pixel.

3. The method of claim 1, wherein the attention mask identifies an area of the avatar that is affected by the physiological signal.

4. The method of claim 1, wherein the attention mask includes an attention weight that is indicative of a strength of the physiological signal.

5. The method of claim 1, wherein the physiological signal is at least one of a blood volume pulse rate, a blinking rate, or a respiratory rate.

6. The method of claim 1, further comprising generating another pixel adjustment value based on the physiological signal, the attention mask, and one or more color coefficients, wherein the color coefficients are specific to the physiological characteristic.

7. The method of claim 6, wherein applying the one or more color coefficients includes generating an alpha mask for each color of the color coefficients and combining the alpha masks to render the avatar.

8. The method of claim 1, wherein the pixel adjustment value is a vector corresponding to a direction and magnitude for one or more pixels.

9. A computer storage media including instructions, which when executed by a processor, cause the processor to:

receive a physiological signal;

generate an attention mask based on the received physiological signal;

generate an alpha mask for a first texture based on the physiological signal and the attention mask; and combine the generated alpha mask for the first texture with an alpha mask of a second texture of an avatar to render the avatar.

10. The computer storage media of claim 9, wherein the attention mask identifies an area of the avatar that is affected by the physiological signal.

11. The computer storage media of claim 9, wherein the physiological signal is at least one of a blood volume pulse rate, a blinking rate, or a respiratory rate.

12. The computer storage media of claim 9, wherein the instructions, when executed by the processor, further cause the processor to:

receive a frame of a video sequence; and render the avatar for the frame of the video sequence.

13. The computer storage media of claim 9, wherein the instructions, when executed by the processor, further cause the processor to receive an external factor affecting at least one of the attention mask or the physiological signal.

14. A system for applying a physiological characteristic to an avatar, the system comprising:

a processor; and memory storing instructions, which when executed by the processor, cause the processor to:

receive a physiological signal;

generate an attention mask based on the received physiological signal;

generate a pixel adjustment value based on the physiological signal and the attention mask; and apply the pixel adjustment value to a pixel in a texture of an avatar.

15. The system of claim 14, wherein:

the pixel adjustment value is a first pixel adjustment value;

the pixel is a first pixel; and the instructions cause the processor to:

generate a second pixel adjustment value based on the physiological signal and the attention mask, wherein the second pixel adjustment value is different than the first pixel adjustment value; and apply the second pixel adjustment value to a second pixel in the texture of the avatar wherein the second identified pixel is different than the first pixel.

16. The system of claim 14, wherein the attention mask identifies an area of the avatar that is affected by the physiological signal.

17. The system of claim 14, wherein the attention mask includes an attention weight that is indicative of a strength of the physiological signal.

18. The system of claim 14, wherein the instructions cause the processor to generate another pixel adjustment value based on the physiological signal, the attention mask, and color coefficients, wherein the color coefficients are specific to the physiological characteristic.

19. The system of claim 18, wherein applying the color coefficients includes generating an alpha mask for each color of the color coefficients and combining the alpha masks render the avatar.

20. The system of claim 18, wherein the instructions cause the processor to:

receive an external factor that affects at least one of the color coefficients, attention mask, or physiological signal; and generate the another pixel adjustment value based on the external factor.

* * * * *